United States Patent [19]

Daussin et al.

[11] Patent Number: 5,185,384
[45] Date of Patent: Feb. 9, 1993

[54] METHOD FOR REDUCING HYDROLYZABLE CHLORIDE IN TOLUENE DIISOCYANATE

[75] Inventors: Rory D. Daussin, Bellaire; Van A. Kent, Lake Jackson; Steven B. Lowenkron, Houston, all of Tex.

[73] Assignee: The Dow Chemical Company, Midland, Mich.

[21] Appl. No.: 647,328

[22] Filed: Jan. 28, 1991

[51] Int. Cl.$^5$ .............................................. C08G 18/70
[52] U.S. Cl. ............................. 521/160; 252/182.20; 252/182.21; 528/67; 560/352
[58] Field of Search ...................... 560/352; 521/160; 528/67; 252/182.20, 182.21

[56] References Cited

U.S. PATENT DOCUMENTS

| | | | |
|---|---|---|---|
| 2,680,127 | 6/1954 | Slocombe et al. | 560/347 |
| 2,822,373 | 2/1958 | Beck | 560/347 |
| 3,140,305 | 7/1964 | Lowenstein | 560/347 |
| 3,179,680 | 4/1965 | Kober | 560/352 |
| 3,219,678 | 11/1965 | Kober et al. | 560/352 |
| 3,264,336 | 8/1966 | Powers | 560/353 |
| 3,373,182 | 3/1968 | Powers | 528/44 |
| 3,405,040 | 10/1968 | Ewald | 203/88 |
| 3,452,073 | 6/1969 | Schultz | 560/351 |
| 3,455,836 | 7/1969 | Schultz et al. | 252/182 |
| 3,457,291 | 7/1969 | Baylor | 560/352 |
| 3,458,558 | 7/1969 | Shing Cheng | 560/352 |
| 3,549,504 | 12/1970 | Adica et al. | 203/49 |
| 3,781,320 | 12/1973 | Irwin | 560/352 |
| 3,816,496 | 6/1974 | Schnabel | 560/352 |
| 3,857,871 | 12/1974 | Hatfield et al. | 560/352 |
| 3,912,600 | 10/1975 | Hatfield et al. | 203/73 |
| 4,076,577 | 2/1978 | Hetzel et al. | 159/47 R |
| 4,118,286 | 10/1978 | Burns et al. | 203/89 |
| 4,138,424 | 2/1979 | Maekawa et al. | 203/88 |
| 4,143,008 | 3/1979 | Zwolinski et al. | 560/352 |
| 4,193,932 | 3/1980 | Yamamoto et al. | 560/347 |
| 4,251,401 | 2/1981 | Reischl | 525/424 |
| 4,251,638 | 2/1981 | Reischl | 521/128 |
| 4,293,456 | 10/1981 | Reischl | 156/62.2 |
| 4,311,800 | 1/1982 | Reischl | 521/109 |
| 4,465,638 | 8/1984 | Kan et al. | 560/340 |
| 4,480,081 | 10/1984 | Rosin et al. | 528/49 |
| 4,489,177 | 12/1984 | O'Connor et al. | 521/164 |
| 4,506,044 | 3/1985 | Raes et al. | 521/137 |
| 4,595,709 | 6/1986 | Reischl | 521/79 |
| 4,604,410 | 8/1986 | Altenberg | 521/172 |
| 4,774,357 | 9/1988 | Keggenhoff et al. | 560/352 |

FOREIGN PATENT DOCUMENTS 1384065 2/1975 United Kingdom ............... 560/352
1458747 12/1976 United Kingdom .

OTHER PUBLICATIONS

CA 93:47803z 1980-May.
CA 93:47804a May 1980.
CA 95:63438f May 1981.
CA 95:98778u Apr. 1981.
CA 105:115886x Jan. 1986.
CA 109:94157a Nov. 1987.
Copending application 07/727,707.
Derwent 90-059484 East German Patent 271820 Sep. 20, 1989.
Derwent 55901S Japanese Patent 71/29,841 Mar. 25, 1969.
Derwent 35349U Dutch Patent 72/15,759 Apr. 6, 1973.
Derwent 68-84069P Dutch Patent 65/14,716 Nov. 12, 1965.
Derwent 89694P British Patent 1,080,717 Aug. 23, 1967.
Derwent 09365U Belgian Patent 786,596 Jan. 22, 1973.

*Primary Examiner*—Maurice J. Welsh
*Assistant Examiner*—Rachel Johnson

[57] ABSTRACT

Disclosed is a method for reducing hydrolyzable chloride in toluene diisocyanate (TDI) and, particularly, in TDI distillation bottoms, and polymers produced using the reduced hydrolyzable chloride bottoms. Crude TDI is heated, optionally in the presence of a solvent, to cause: (a) partial reflux, (b) partial reflux and fractionation, or (c) complete reflux and fractionation; under conditions sufficient to reduce hydrolyzable chloride. After distilling the crude TDI to form TDI monomer, the bottoms produced are thereby desirably reactive and viscosity-stable over a significant period of time. The treated bottoms can be reacted with compounds containing active hydrogen containing groups to form polyurethane, polyurea, and polyisocyanurate polymers, particularly foams.

12 Claims, No Drawings

METHOD FOR REDUCING HYDROLYZABLE CHLORIDE IN TOLUENE DIISOCYANATE

BACKGROUND OF THE INVENTION

This invention relates to a composition of reactive toluene diisocyanate bottoms and a method of producing them. More particularly, this invention relates to reduction of hydrolyzable chloride in crude toluene diisocyanate.

The term "hydrolyzable chloride" refers to labile chlorine atoms which are free, ionically or covalently bonded within a compound, but have more ionic character than, for example, the chlorine atom present in chlorobenzene. Hydrolyzable chloride concentration may also be referred to as chloride equivalent or chloride level.

Toluene diisocyanates (hereinafter TDI) are commonly prepared by phosgenation of toluene diamines. Typical processes for the phosgenation of amines may be found in U.S. Pat. Nos. 2,680,127: 2,822,373: and 3,781,320. After the phosgenation of toluene diamines to form TDI, the product diisocyanate is generally distilled from the reaction mixture in which it is prepared. This reaction product mixture, after phosgenation but prior to distillation of TDI monomer, shall hereafter be referred to as crude TDI. At the conclusion of the distillation, the residue of the distillation is commonly referred to as distillation bottoms or, more simply, just bottoms. The bottoms normally contain a quantity of high boiling residue composed of materials such as alpha and omega-isocyanato-biurets, polycarbodiimides, diisocyanatocarbodiimides, polyuretidinediones, isocyanurates and various other isocyanate adducts, including hydrolyzable chloride containing compounds. This residue is typically discarded.

The disposal of this residue is a serious problem to the TDI industry. It is costly and poses safety problems. The handling of this material is a problem because special equipment is needed to move and store it prior to disposal.

A number of processes for reduction of hydrolyzable chloride have been developed, primarily for methylene diphenyl diisocyanate. Some of the processes involve reduction of acidity levels. U.S. Pat. No. 3,179,680 (Inventor: Kober: Assignee: Mathieson Chemical Corp ) discloses that the concentration of hydrolyzable chloride in organic isocyanates may be reduced by heating the organic isocyanates in the presence of small amounts of water. However, water is reactive with isocyanates and may reduce yields or cause other processing problems. U.S. Pat. No. 3,219,678 (Inventor: Kober: Assignee: Mathieson Chemical Corp.) discloses that reduction of hydrolyzable chloride can be achieved by heating an isocyanate containing hydrolyzable chloride at temperatures considerably above those required and used for the cleavage of carbamoyl chlorides to form organic isocyanates and hydrogen chloride (hereinafter HCl), and then, passing an inert gas through the isocyanate to remove the HCl. This process, however, fails to address the problem of reformation of hydrolyzable chloride containing compounds. U.S. Pat. No. 3,857,871 (Inventor: Hatfield et al.: Assignee: The Upjohn Co.) discloses that acidity and hydrolyzable chloride levels of polymethylene polyphenyl polyisocyanate (hereinafter PMDI) are reduced and reactivity increased by exposing the polyisocyanate in a liquid state at 350° F. to 450° F. to countercurrent treatment with an inert gas. However, use of heat and an inert gas alone does not appear to maximize removal of hydrolyzable chloride to produce desirably reactive TDI bottoms. Thus, it would be desirable to remove sufficient hydrolyzable chloride from crude TDI to produce both reduced hydrolyzable chloride TDI monomer and commercially useful distillation bottoms.

SUMMARY OF THE INVENTION

In one aspect, the invention is a method for reducing hydrolyzable chloride in crude TDI comprising heating crude TDI under conditions sufficient to (a) partially reflux, (b) partially reflux and fractionate, or (c) completely reflux and fractionate the crude TDI. The crude TDI may be admixed with a solvent or not. Heating the crude TDI serves to alter the equilibrium of the decomposition and reformation of hydrolyzable chloride containing compounds to promote decomposition of hydrolyzable chloride containing compounds into volatile chloride containing compounds. The partial or complete refluxing with fractionation, or partial refluxing alone, of the crude TDI serves to remove the volatile chloride containing compounds from the crude TDI.

The utility of this invention is to produce low hydrolyzable chloride crude TDI which may be distilled to produce both low hydrolyzable chloride TDI monomer and also TDI distillation bottoms which are viscosity-stable and sufficiently reactive to be commercially useful.

In another aspect, this invention is a composition for use in preparing a polyurea, polyurethane, or polyisocyanurate material comprising reactive and viscosity-stable TDI bottoms from distillation of low hydrolyzable chloride crude TDI.

In still another aspect, this invention is a polymer prepared from a formulation comprising (a) an active hydrogen compound and (b) a polyisocyanate component containing from about 1 to about 100 weight percent, based on total weight of polyisocyanate component, of the low hydrolyzable chloride TDI distillation bottoms of this invention.

DESCRIPTION OF THE PREFERRED EMBODIMENTS

It is known in the art that at least some hydrolyzable chloride containing compounds, in crude TDI, will disassociate into HCl and isocyanates when heated. Reduction of hydrolyzable chloride in crude TDI may be achieved by decomposing hydrolyzable chloride containing compounds, in the crude TDI, into volatile chloride containing compounds and removing those volatile chloride containing compounds from the crude TDI. These volatile chloride containing compounds include at least HCl, but may include other compounds as well. Discussion herein will be limited to HCl, but it will be understood that the method of the invention is applicable to all these chloride containing compounds.

In this invention, crude TDI is heated, with or without a solvent, sufficiently to cause partial reflux, partial reflux with fractionation, or complete reflux with fractionation. A liquid is completely refluxed by 1) heating the liquid to boiling, 2) passing the gases and vapor into a condenser, 3) condensing substantially all of the non-gaseous components and 4) returning the condensate to the boiling liquid. Partial reflux of a liquid is achieved by the same procedure except that a portion of the vapor is released from the system.

The concept of chemical equilibrium is well known in the art. For the purposes of the present invention, stated briefly, equilibrium is the propensity of chemical compounds to exist not as pure materials, but rather as mixtures of products and their reactants. In other words, equilibrium is the state at which the rate of formation is equal to the rate of decomposition.

The method of this invention involves affecting one and preferably two equilibria. One of these is the equilibrium of decomposition of hydrolyzable chloride containing compounds, in crude TDI, into HCl and isocyanates. The other is the solubility equilibrium of gaseous HCl in refluxing vapor.

Stated very generally, the method of this invention includes removing HCl from a crude TDI system, thereby reducing hydrolyzable chloride. Since HCl and hydrolyzable chloride containing compounds are in equilibrium, removing the HCl promotes further decomposition of hydrolyzable chloride containing compounds, thereby producing more HCl. Continuing this process for a sufficient time period produces a crude TDI with a relatively low concentration of hydrolyzable chloride. After distillation of TDI monomer, the distillation bottoms formed will preferably be desirably reactive and viscosity-stable.

However, before HCl may be removed from a crude TDI system and thereby affect the equilibrium of decomposition and reformation of hydrolyzable chloride containing compounds, there must be enough HCl present to be acted upon by a means of removal. At ambient temperatures, this equilibrium favors the production of hydrolyzable chloride containing compounds to such a great extent, that only a very small concentration of free HCl is present.

One part of the method of this invention incorporates, in general, applying heat to crude TDI to increase the equilibrium concentration of HCl. The preferred temperature range is from about 40° C. to about 230° C., but preferably from about 150° C. to about 200° C., and more preferably from about 180° C. to about 195° C.

Another part of this invention, applied concurrently with the heating aspect, incorporates increasing removal of HCl from crude TDI. This invention includes application of any one of three means to remove HCl from crude TDI. Those means are: 1) partial reflux, 2) partial reflux with fractionation, and 3) complete reflux with fractionation. Where the means to remove HCl from the refluxing crude TDI includes fractionation, HCl removal is increased by affecting the solubility equilibrium of gaseous HCl in the refluxing vapor. Fractionating refluxing vapor increases separation of gaseous HCl from refluxing vapor. Where the means of removal of HCl from refluxing crude TDI includes a partial reflux, HCl removal is increased by a gradual loss of refluxing vapor.

Refluxing, either partial or complete, with fractionation, or partial refluxing, of crude TDI, should continue until bottoms produced from the crude TDI are desirably reactive. Preferably, this treatment is continued until sufficient hydrolyzable chloride is removed from the crude TDI such that, after distillation, the bottoms have a hydrolyzable chloride concentration of less than about 1200 ppm hydrolyzable chloride, preferably less than about 1000 ppm hydrolyzable chloride, and more preferably less than about 750 ppm hydrolyzable chloride.

Complete reflux and fractionation of an admixture of crude TDI with a solvent is a preferred embodiment of this invention. Refluxing the admixture with fractionation causes effective separation of HCl from the refluxing vapors sufficient to produce crude TDI with significantly reduced hydrolyzable chloride. The reduced hydrolyzable chloride crude TDI of this invention is distilled to produce reduced hydrolyzable chloride TDI monomer and also distillation bottoms which are preferably both reactive and viscosity-stable.

In another embodiment, crude TDI is not admixed with a solvent, but instead is subjected to a complete reflux and fractionation without solvent. Care should be exercised that the temperatures used to cause reflux and fractionation do not also cause undesirable side reactions.

In still another embodiment, crude TDI, either with or without admixture with a solvent, is subjected to a partial reflux. The removal of uncondensed vapor serves to effect removal of sufficient HCl from crude TDI to produce reactive TDI distillation bottoms. A combination of partial refluxing and fractionation of crude TDI, with or without admixture of the crude TDI with a solvent, is also an embodiment of the present invention.

Any crude TDI is suitable for use in this invention. The crude TDI used with this invention is preferably formed by the phosgenation of toluene diamine to form crude TDI as described above. However, crude TDI from any source is suitable.

A solvent suitable for use with this invention can be selected by evaluation of two criteria. First, the solvent should dissolve or suspend crude toluene diisocyanate. Second, the solvent should be an effective means to remove HCl from crude TDI when refluxed, with or without fractionation, with TDI as a solvent admixture. That is, the solvent should be sufficiently compatible with HCl such that the solvent will remove HCl from crude TDI. However, the solvent should not be so highly compatible that, once admixed, the solvent and HCl cannot be separated. Chlorobenzene and ortho-dichlorobenzene are examples of effective solvents for use with this invention.

Determination of hydrolyzable chloride can be done according to the procedure described below. Hydrolyzable chloride can be determined by liberating ionic chloride from the isocyanate and titrating the resulting chloride ion concentration with, for example, silver nitrate. An admixture of a known weight of isocyanate and a mixture of 50 parts by weight toluene, 50 parts by weight methanol, and 6.5 parts by weight pyrrolidine is first prepared in a quantity sufficient to react with the diisocyanate and dissolve the products of the reaction therewith. A solution is formed by stirring the admixture for about four minutes. A quantity of about 4 ml concentrated nitric acid (85 weight percent), sufficient to maintain activity of silver/silver chloride electrodes used to determine the end point of titration, is added. The solution is stirred for about one additional minute. The electrodes are inserted and titration with a dilute solution (e.g., 0.025 Normal (N)) of silver nitrate is begun. Titration is ended when an inflection point is determined. The concentration of hydrolyzable chloride is calculated from the amount of silver nitrate consumed.

Both crude TDI and the distillation bottoms generally contain acidic materials left over from the phosgenation process. The term "acid", as used herein, refers to these contaminants as well as to free HCl and/or labile covalently bonded chlorides present in the isocyanate, such as carbamoyl chlorides and others, that respond as acids in standard analytical tests.

The acid content or level, of crude TDI and TDI distillation bottoms, is readily determined by standard analytical tests such as ASTM D-4667-87 or other tests for acidity. These tests generally involve heating the isocyanate in a solution of mixed alcohols or toluene and methanol, and titrating the resulting mixture with dilute potassium hydroxide. Acidity is expressed as weight percent HCl.

Crude TDI is distilled to prepare TDI monomer and distillation bottoms. For this invention, the crude TDI is preferably distilled by means of a falling film evaporator, but may be prepared in any manner. Both the TDI monomer and distillation bottoms prepared by the method of this invention have reduced hydrolyzable chloride compared to those prepared by distillation of untreated crude TDI.

The TDI distillation bottoms of this invention, prepared by distilling the treated crude TDI, are preferably reactive. For the purposes of this invention, the term "reactive" is defined as the ability of the TDI bottoms to advantageously react with a compound containing an active hydrogen containing group. Any suitable organic compound containing an active hydrogen containing group, as determined by the Zerewitinoff method, may be used for reaction with the distillation bottoms or blends thereof with other polyisocyanates. Active hydrogen compounds are compounds having hydrogen-containing functional groups which will react with an isocyanate group. The Zerewitinoff test described by Kohler in the *Journal of the American Chemical Society*, Vol. 49, page 3181 (1927) predicts the tendency of a hydrogen-containing group to react with isocyanates.

When PMDI materials are blended with TDI distillation bottoms, these blends are preferably at least as reactive as the starting PMDI materials. This reactivity can be determined by measuring the time from mixing of an isocyanate or an admixture of isocyanates with an active hydrogen compound until specific phenomena are observed in a forming polyurethane or polyisocyanurate foam. Materials containing a high concentration of hydrolyzable chloride, some or all of which may be in the form of acidity, tend to either not foam at all, or to fail to timely cure, with the result that they remain tacky. The measurements of foam forming ability include:

a) Cream time: the time in seconds from mixing until foaming begins, determined by observing when gas first begins to separate from the admixture:
b) Gel time: the time in seconds from mixing until the foaming admixture first begins to produce "strings" adhering to a wooden spatula quickly inserted and removed from the foaming admixture:
c) Tack-free time: the time in seconds from mixing until the foam surface loses its sticky quality. Reactive bottoms are those that can be readily made into foam with suitably fast cream, gel, and tack-free times.

Active hydrogen components most commonly used in polyurethane production are those compounds having at least two hydroxyl groups. Those compounds are referred to herein as polyols. Representatives of suitable polyols are generally known and are described in such publications as *High Polymers*, Vol. XVI, "Polyurethanes, Chemistry and Technology" by Saunders and Frisch, Interscience Publishers, New York, Vol. I, pp. 32–42, 44–54 (1962) and Vol. II, pp. 5–6, 198–199 (1964); *Organic Polymer Chemistry* by K. J. Saunders, Chapman and Hall, London, pp. 323–325 (1973): and *Developments in Polyurethanes*. Vol. I, J. M. Burst, ed., Applied Science Publishers, pp. 1–76 (1978).

Typical polyols include polyester polyols, polyester amide polyols, and polyether polyols having at least two hydroxyl groups. Polyethers and polyesters having hydroxyl terminated chains are preferred for use as relatively high molecular weight active hydrogen containing compounds for use in forming polyurethanes in particular. Examples of polyols also include hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers, including polythioethers and acetals, such as polyacetals. Aminated polyols may also be used.

The amount of TDI monomer present in the bottoms is a function of the producing unit's ability to handle the bottoms as their viscosity increases with time. Units which can quickly dispose of the bottoms are able to distill more TDI monomer from the crude TDI than units which must hold the bottoms for a significant time period prior to disposal. Bottoms produced by the method of this invention contain less than about 50 percent, preferably less than about 25 percent of TDI monomer.

The low hydrolyzable chloride TDI bottoms of this invention are desirably reactive and viscosity-stable. Untreated TDI distillation bottoms quickly increase in viscosity. Advantageously, the bottoms produced by the method of the present invention will, by comparison, increase in viscosity more slowly and/or to a lesser extent than untreated bottoms. The viscosity stability of the distillation bottoms may be determined by evaluating changes in viscosity beginning immediately after they are prepared. Distillation bottoms may be considered viscosity-stable if their viscosity in centipoise, as measured by ASTM-D445-88, no more than doubles ($\leq 100$ percent increase) within the first 3 hours, preferably within the first 4 hours, and more preferably within the first 5 hours of the conclusion of the distillation from which the bottoms resulted, when the bottoms contain about 25 percent TDI monomer and are stored at about 100° C.

The TDI distillation bottoms prepared using the method of the present invention are suitably used without dilution, for instance, to prepare a foam. However, the bottoms can be blended with another polyisocyanate different from the distillation bottoms in an amount sufficient to achieve a preselected viscosity and/or a desired reactivity as evidenced by the ability to form a polymeric foam and the qualities of the foam formed. The polyisocyanate used for dilution is suitably any, preferably liquid, organic isocyanate compound having an average of more than one isocyanate group per molecule. The polyisocyanate is suitably crude or distilled, but preferably has a viscosity less than that of the TDI distillation bottoms. Such polyisocyanate compounds are well known and readily available commercially.

Examples of suitable polyisocyanates include aromatic, aliphatic and cycloaliphatic polyisocyanates and combinations thereof. Representative polyisocyanates include diisocyanates such as m-phenylene diisocyanate, toluene-2,4-diisocyanate, toluene-2,6-diisocyanate, hexamethylene-diisocyanate, tetra-methylene-diisocyanate, cyclohexane-1,4-diisocyanate, hexahydrotoluene diisocyanate and isomers thereof, 1-methoxyphenyl-2,4-diisocyanate, diphenylmethane-4,4'-diisocyanate, diphenylmethane-2,4'-diisocyanate, 3,3'-dimethyl-4,4'-biphenyl diisocyanate, 3,3'-dimethyl-diphenyl-methane-4,4'-diisocyanate and the like; triisocyanates such as 4,4', 4''-triphenylmethane triisocyanate, toluene-2,4,6-triisocyanate, and the like: tetraisocyanates such as 4,4'-dimethyldiphenylmethane-2,2 ', 5,5'-tetraisocyanate, 4,4'-dicyclohexanediisocyanate, isophorone diisocyanate, isomers of each and the like: other polyisocyanates such as polyphenylisocyanate and the like: and mixtures thereof. TDI, diphenylmethane-4,4'-diisocyanate, diphenylmethane2,4'-diisocyanate and PMDI materials are preferred because of their availability and properties. Mixtures of polyisocyanate components are particularly preferred.

PMDI materials are preferred for use in the practice of the invention. PMDI materials are mixtures containing from about 35 to about 85, preferably from about 65 to about 75, percent by weight of methylene diphenyl diisocyanate, the remainder of the mixture being closely related polyisocyanates of higher molecular weight and functionality greater than about two. They are well-known compositions, and are commercially prepared by phosgenation of mixtures of the corresponding methylene-bridged polyphenyl polyamines. Polyisocyanates suitable for use in the practice of the invention include those available commercially from The Dow Chemical Company under the trade designation PAPI ®.

Blends of the invention are composed of from about 1 to about 99 percent by weight TDI bottoms, and the remainder polyisocyanate. From about 90 to about 99 weight percent bottoms based on total weight of a blend are suitably used; however, preferably, the bottoms blend contains at least about 10, more preferably from about 20 to about 75, and most preferably from about 20 to about 40 weight percent bottoms based on total weight of the blend. The relative proportions of bottoms and polyisocyanate are generally selected to achieve a preselected viscosity and preselected properties in resulting products. Advantageously, the relative proportions of bottoms and polyisocyanate are selected to achieve a viscosity suitable for a use of the blend.

Advantageously, for use in making foams, the blend has a viscosity of less than about 10,000 centipoise, preferably from about 30 to about 3,000 centipoise, more preferably from about 40 to about 2,500 centipoise. When a blend is to be used for a specific application, the viscosity is most preferably preselected for convenience in preparing that type of material by processes known to those skilled in the art. For instance, in the case of insulative polyurethane foams, viscosity is generally preferably from about 200 to about 3,000 cps.

When bottoms are to be used in applications sensitive to specific levels of acidity, care should be exercised that only those distillation bottoms with an appropriate acidity concentration are used. Where an application requires such an isocyanate, then bottoms having acidity of no more than about 500 ppm are preferably blended with isocyanates having less acidity such that the blend has less than about 400 ppm, preferably less than about 300 ppm, acidity.

Blends of the distillation bottoms and liquid polyisocyanates are suitably used to make polyisocyanurate, polyurethane, polyurea, and polyurethane-polyurea polymers and the like. The polymers suitably take the form of products such as flexible or rigid foams, adhesives, binders and the like. Polyisocyanurate foams are foams formed using a ratio of isocyanate groups to active hydrogen groups of at least about 1.3, preferably, in the presence of trimerization catalysts. Polyurethane foams are formed when little trimerization of isocyanate takes place, and polymer formation is primarily the reaction of active hydrogen groups of an active hydrogen component with isocyanate groups of a polyisocyanate component.

The distillation bottoms of the present invention are advantageously reacted with active hydrogen compounds in the presence of a blowing agent. Any blowing agent or mixture thereof is suitable for use in the practice of the invention. Suitable blowing agents include inorganic blowing agents such as water, organic blowing agents which are volatile at reaction temperatures and dissolved inert gases. Suitable organic blowing agents include acetone: ethyl acetate: methanol: ethanol: halogen-substituted alkanes such as methylene chloride, chloroform, ethylidene chloride, vinylidene chloride, monofluorotri-chloromethane, chlorodifluoromethane, dichlorodi-fluoromethane and the like: butane: hexane: heptane: diethyl ether: and the like. Gases inert to the starting components such as nitrogen, air, carbon dioxide and the like are also useful blowing agents. Compounds, such as azides, which decompose at suitable temperatures to produce gases such as nitrogen are also useful. Preferred blowing agents are compounds which boil between about −50° and 100° C., more preferably between about 0° and 50° C.

The amount of blowing agent employed is not critical to the invention, but is preferably sufficient to foam the reaction mixture. The amount will vary with factors such as the density desired in a foamed product.

Water is a useful blowing agent for use in the practice of the invention. In addition to generating carbon dioxide gas for foaming, water reacts quickly with polyisocyanate components, thus contributing to early polymer strength needed for gas retention. Generally, when water is used, it is present in proportions of from about 1.5 to about 8 weight percent of water based on total weight of active hydrogen components. Other blowing agents, can be used with water.

Rigid polyisocyanurate and polyurethane foams prepared from the distillation bottoms of the present invention are particularly useful. Those skilled in the art of preparing such foams can readily use the TDI distillation bottoms of the invention, or blends thereof, with other polyisocyanates, to prepare the foams.

Methods known to those skilled in the art can suitably be used to prepare a rigid polyisocyanurate foam using the TDI bottoms, or blends thereof, with other polyisocyanates. For instance, the process of U.S. Pat. No. 4,604,410, can be followed, substituting the distillation bottoms, or blends of the invention, for other polyisocyanates. Preferably, the distillation bottoms, or blends of the invention, are reacted with a polyfunctional active hydrogen compound, in the presence of a catalyst, which catalyzes the formation of isocyanurates, and a blowing agent suitable for forming foams having preselected physical properties.

Suitable catalysts are those which catalyze the formation of isocyanurates such as those mentioned in *High Polymers.* Vol. XVI, "Polyurethanes, Chemistry and Technology" by Saunders and Frisch, Interscience Publishers, New York, part 1, pp. 94–97 (1962). Such catalysts are referred to herein as trimerization catalysts. Examples of these catalysts include aliphatic and aromatic tertiary amine compounds, organometallic compounds, alkali metal salts of carboxylic acids, phenols and symmetrical triazine derivatives. Preferred catalysts are potassium salts of carboxylic acids such as potassium octoate and tertiary amines such as, for instance, 2,4,6-tris(dimethyl aminomethyl) phenol.

The following examples and comparative examples serve to illustrate the present invention. These examples are included for illustrative purposes only and are not intended to limit the scope of the invention.

EXAMPLE 1

A complete reflux and fractionation of crude TDI is carried out by placing about 600 ml of a 10 percent crude TDI and 90 percent o-dichlorobenzene solution in a 1000 ml three-necked flask. A one-foot vacuum jacketed Vigreux column is placed on the central neck of the flask for fractionation. A water cooled West condenser is placed on top of the Vigreux column for reflux. The solution is heated to 185° C. in about 18 minutes. The temperature is maintained at about 186° C. for the remainder of the experiment. Overhead vapors are condensed in the West column and returned to the flask through the Vigreux column. Samples are taken at 8 minute intervals and analyzed for hydrolyzable chloride. At the beginning of this experiment, the hydrolyzable chloride concentration of the crude TDI, corrected for dilution, is 12,093 ppm. After 72 minutes, the concentration of hydrolyzable chloride is 916 ppm.

EXAMPLE 2

A partial reflux is carried out by repeating the procedure of Example 1 substantially identically except that overhead vapors are condensed and removed from the system. At the beginning of this experiment, the crude TDI has a hydrolyzable chloride concentration, corrected for dilution, of 12,021 ppm. After 72 minutes, the concentration of hydrolyzable chloride is 831 ppm.

COMPARATIVE EXAMPLE 3

A complete reflux with no fractionation is carried out by repeating the procedure of Example 1 substantially identically except that the Vigreux column is not used. At the beginning of this experiment, the crude TDI has a hydrolyzable chloride concentration, corrected for dilution, of 11,905 ppm. After 72 minutes, the concentration of hydrolyzable chloride is 1,565 ppm.

EXAMPLE 4

Crude TDI prepared according to Example 1 is distilled to form TDI monomer and distillation bottoms, the bottoms containing about 22.3 percent TDI monomer. The distillation bottoms are stored at 100° C. and viscosity is measured periodically. Viscosity growth is shown in the Table.

COMPARATIVE EXAMPLE 5

The materials and procedures of Example 4 are repeated substantially identically except that untreated distillation bottoms are used in place of the treated distillation bottoms, and the bottoms contain about 25.1 percent TDI monomer. Viscosity growth is shown in the Table.

EXAMPLE 6

A foam is prepared by mixing 100 parts of an "A" component composed of 75 parts PMDI and 25 parts TDI bottoms bottoms as prepared in example 4, with 118 parts of a "B" component prepared using a polyurethane foam formulation compromising polyether and amine polyols, catalysts, surfactants, and water and trichlorofluoromethane as blowing agents. This foam has

TABLE OF RESULTS FOR EXAMPLE 4 & COMPARATIVE EXAMPLE 5

| Minutes Following Preparation 100° C. | Example 4 Centipoise | Comparative Example 5 Centipoise |
|---|---|---|
| 0 | 105.5 | 35.8 |
| 10 | 136.9 | 45.1 |
| 20 | 140.3 | 46.8 |
| 40 | 150.0 | 51.1 |
| 102 | 174.5 | 68.5 |
| 197 | 193.5 | 96.1 |
| 300 | 208.9 | 152 |
| 644 | 239.8 | 956.8 |
| 1432 | 287.3 | ** |

**indicates that the material would not flow through the viscometer a cream time of 3 seconds, a gel time of 23 seconds a tack-free time of 30 seconds.

COMPARATIVE EXAMPLE 7

A foam is prepared using the formulation and method of Example 8 except that 100 parts of PMDI and no TDI distillation bottoms are used to prepare the "A" component. This foam has a cream time of 4 seconds, a gel time of 23 seconds, and a tack-free time of 33 seconds.

COMPARATIVE EXAMPLE 8

An attempt is made to prepare a foam using the formulation and method of Example 8 except that the "A" component is prepared using 25 parts of untreated TDI bottoms and 75 parts PMDI. The reaction mixture does not produce sufficient heat to vaporize the blowing agent and therefore does not foam.

What is claimed is:

1. A method for reducing hydrolyzable chloride in crude toluene diisocyanate comprising subjecting crude toluene diisocyanate containing hydrolyzable chloride to (a) a partial reflux, (b) a partial reflux and fractionation, or (c) a complete reflux and fractionation, under conditions sufficient to form a product crude toluene diisocyanate having reduced hydrolyzable chloride.

2. The method of claim 1 wherein the crude toluene diisocyanate is admixed with a solvent prior to heating.

3. The method of claim 2 wherein the solvent is chlorobenzene or ortho-dichlorobenzene.

4. A method for reducing hydrolyzable chloride in crude toluene diisocyanate comprising heating crude toluene diisocyanate admixed with orthodichlorobenzene, at a temperature of from about 180° C. to about 195° C., under conditions sufficient to cause complete refluxing and, concurrently, fractionating the refluxing admixture for a period of time sufficient to reduce hydrolyzable chloride in the crude toluene diisocyanate to a concentration such that, after distillation of toluene diisocyanate monomer, the toluene diisocyanate distillation bottoms produced have (a) a hydrolyzable chloride concentration of less than about 1000 ppm, (b) a toluene diisocyanate monomer concentration of less than about 50 percent, and (c) a viscosity growth rate of no more than about 100 percent measured 3 hours after completion of the distillation step when the bottoms contain about 25 percent toluene diisocyanate monomer and are stored at about 100 ° C.

5. A composition for use in preparing a polyurea, polyurethane, or polyisocyanurate polymer comprising toluene diisocyanate bottoms prepared by distillation of reduced hydrolyzable chloride crude toluene diisocyanate prepared by the method of claim 1.

6. A method for preparing toluene diisocyanate bottoms suitable for use in preparing a polyurea, polyurethane, or polyisocyanurate polymer comprising distilling reduced hydrolyzable chloride crude toluene diisocyanate, prepared by the method of claim 1, to produce toluene diisocyanate bottoms.

7. In a method for reducing hydrolyzable chloride in crude toluene diisocyanate by heating and completely refluxing the crude toluene diisocyanate admixed with a solvent to produce an admixture vapor, an improvement comprising fractionating the refluxing admixture vapor.

8. A polymer prepared by reacting a reaction mixture comprising a components:

(A) an active hydrogen compound and
(B) a polyisocyanate component containing from about 1 to about 100 weight percent, based on total weight of polyisocyanate component, of reactive toluene diisocyanate distillation bottoms prepared by the method of claim 6.

9. The polymer of claim 8 wherein the polymer is a foam and the reaction mixture further comprises a blowing agent, or a blowing agent and a catalyst.

10. The polymer of claim 9 wherein the toluene diisocyanate distillation bottoms are from about 10 to about 90 weight percent of polyisocyanate component (B).

11. The polymer of claim 9 wherein the toluene diisocyanate distillation bottoms are from about 20 to about 75 weight percent of polyisocyanate component (B).

12. The polymer of claim 9 wherein the toluene diisocyanate distillation bottoms are from about 20 to about 40 weight percent of polyisocyanate component (B).

* * * * *